United States Patent
Fujita et al.

(10) Patent No.: US 7,354,397 B2
(45) Date of Patent: Apr. 8, 2008

(54) CAPSULE-TYPE MEDICAL APPARATUS AND A COMMUNICATION METHOD FOR THE CAPSULE-TYPE MEDICAL APPARATUS

(75) Inventors: Manabu Fujita, Hino (JP); Masatoshi Homan, Hino (JP); Motoo Azuma, Tokorozawa (JP); Kaoru Kotouda, Fussa (JP)

(73) Assignee: Olympus Corporation, Tokyo (JP)

( * ) Notice: Subject to any disclaimer, the term of this patent is extended or adjusted under 35 U.S.C. 154(b) by 80 days.

(21) Appl. No.: 10/271,696

(22) Filed: Oct. 16, 2002

(65) Prior Publication Data
US 2003/0213495 A1 Nov. 20, 2003

(30) Foreign Application Priority Data
May 15, 2002 (JP) .............................. 2002-140606

(51) Int. Cl.
*A61B 1/04* (2006.01)

(52) U.S. Cl. ...................... 600/109; 600/101; 600/114; 600/117; 600/118; 600/160; 606/1; 356/241.6

(58) Field of Classification Search ................ 600/109, 600/114–115, 117, 118, 160; 901/1; 606/1
See application file for complete search history.

(56) References Cited

U.S. PATENT DOCUMENTS

| 5,604,531 A | | 2/1997 | Iddan et al. | |
|---|---|---|---|---|
| 5,651,780 A | * | 7/1997 | Jackson et al. | 606/1 |
| 6,709,387 B1 | * | 3/2004 | Glukhovsky et al. | 600/109 |
| 2001/0051766 A1 | * | 12/2001 | Gazdzinski | 600/309 |
| 2002/0032435 A1 | * | 3/2002 | Levin | 606/1 |
| 2002/0103417 A1 | * | 8/2002 | Gazdzinski | 600/109 |
| 2002/0198439 A1 | * | 12/2002 | Mizuno | 600/109 |

FOREIGN PATENT DOCUMENTS
JP 2-31738 2/1990

* cited by examiner

*Primary Examiner*—Linda C. M. Dvorak
*Assistant Examiner*—Matthew J. Kasztejna
(74) *Attorney, Agent, or Firm*—Scully, Scott, Murphy & Presser, P.C.

(57) ABSTRACT

When a capsule is manufactured, a unique number such as a serial number is stored in non-volatile memory in the capsule. If the capsule is used with an external apparatus, the unique number is sent from the capsule to the external apparatus. The external apparatus relates each unique number with a capsule ID comprising a small number of bits in a management table formed in non-volatile memory and sends the capsule ID to the capsule, and the capsule ID with the small number of bits is set as an identifier in the capsule. In this manner, it is made unnecessary to provide a switch in the capsule for setting the identifier and it becomes possible to reduce and send the quantity of information sent as the identifier.

18 Claims, 10 Drawing Sheets

FIG.1

FIG.2A  INITIAL STATE

FIG.2B  AFTER QUERY

FIG.2C  AFTER CONNECTION (AFTER SETTING CAPSULE ID IS COMPLETE)

FIG.2D  AFTER QUERY

FIG.2E  AFTER CONNECTION (AFTER SETTING CAPSULE ID IS COMPLETE)

FIG.3A

| CODE | COMMAND (ORDER) |
|------|-----------------|
| 01 | QUERY |
| 02 | NOTIFICATION OF UNIQUE NUMBER |
| 03 | REQUEST CONNECTION |
| 04 | NOTIFICATION OF COMPLETED CONNECTION |
| 05 | SET CAPSULE ID |
| 06 | NOTIFICATION OF COMPLETED SETTING |
| 07 | INSTRUCTION TO START IMAGE CAPTURING |

| CODE | COMMAND (ORDER) |
|---|---|
| 01 | QUERY |
| 02 | NOTIFICATION OF UNIQUE NUMBER |
| 03 | REQUEST CONNECTION |
| 04 | NOTIFICATION OF COMPLETED CONNECTION |
| 05 | SET CAPSULE ID |
| 06 | NOTIFICATION OF COMPLETED SETTING |
| 07 | INSTRUCTION TO START IMAGE CAPTURING |
| 08 | CLEAR CAPSULE ID |
| 09 | COMPLETION OF CLEARING CAPSULE ID |

| CODE | COMMAND |
|------|---------|
| 01 | QUERY |
| 10 | NOTIFICATION OF POWERING ON |

| TYPE | CODE | PARAMETER |
|------|------|-----------|
| ↑ | ↑ | ↑ |
| 01 | 10 | UNIQUE NUMBER |

CAPSULE-TYPE MEDICAL APPARATUS AND A COMMUNICATION METHOD FOR THE CAPSULE-TYPE MEDICAL APPARATUS

This Application claims benefit of Japanese Patent Application No. 2002-140606 filed in Japan on May 15, 2002, the contents of which are incorporated by this reference.

BACKGROUND OF THE INVENTION

1. Field of the Invention

The present invention relates to a capsule-type medical apparatus, comprising a capsule body which is inserted in a living body to perform observation or the like and an external apparatus, and a communication method for the capsule-type medical apparatus.

2. Description of the Related Art

The latest medical apparatuses include conventional capsule-type medical apparatuses made so as to attain living-body information by having the patient swallow a capsule and to send that living-body information to an external apparatus.

Of these, the U.S. Pat. No. 5,604,531 proposes an in vivo video camera system wherein an image pickup element is placed in a living body and sends the captured images of the digestive tract to outside of the living body. Also, Japanese Patent Laid-open Publication No. H02-31738 discloses a medical capsule constituted to execute prescribed functions inside the living body according to commands from an external apparatus. This medical capsule provides means for identifying each of the capsules when a single patient swallows a plurality of capsules. Also, it is shown that the medical capsules can be used even in the case where a plurality of patients in a single room have each a swallowed capsule.

In the capsule-type medical apparatus, the capsule and the external apparatus for receiving and accumulating data from the capsule are paired once, and then that pairing must be maintained until the examination is ended. In this capsule-type medical apparatus, it is necessary to make a connection with the original partner in the case where the communication connection between the capsule and external apparatus is broken for any reason (a situation wherein the external apparatus must be separated from the living body during the examination). In this case, a connection must not be made with a capsule swallowed by another neighboring person.

With a wireless modem using the 429 MHz band, for example, instead of a capsule-type medical apparatus, the wireless instruments are provided with a switch for setting its own identifier that is constituted so that communicating partners are identified each other.

By the way, when the data sent from the capsule are image data, it is not necessarily the case that images of all internal organs are to be captured after the capsule is swallowed. When the capsule contains a battery, it is desirable to photograph and perform wireless sending of the photographed image signal only when the capsule arrives at the internal organ that is the destination. Also, it is necessary to alter the photographing interval according to the speed of movement of the capsule.

Sending control commands from the external apparatus to the capsule to control the capsule from outside the living body has been considered as means therefor, but it would be necessary to control each specific capsule and to set the identifier for each capsule. However, when considering the application of the abovementioned wireless modem to a capsule-type medical apparatus, it is substantially impossible to establish a switch for setting the identifier in the capsule because of size limitations and the necessity for ensuring that the capsule be watertight.

Another idea considered was writing the abovementioned identifier to non-volatile electronic memory at the time when the capsule is produced. However, in the case where the capsules are shipped in large quantities, the number of digits of the identifier becomes too great. When the number of digits of the identifier becomes too great in this way, the transmission efficiency will drop because the identifier must be placed in the packet header for each packet. Furthermore, a large amount of power will be consumed in the transmission of the identifier portion on the capsule side. Improvements are desired in view of the lifespan of the small battery placed within the capsule.

SUMMARY OF THE INVENTION

It is an object of the present invention to provide a capsule-type medical apparatus and a communication method for the capsule-type medical apparatus, which make the capsule-side switch for setting the identifier unnecessary, reduce the amount of information to be sent as the identifier, and make it possible to send control commands from an external apparatus to a specific capsule.

Also, it is an object of the present invention to provide a capsule-type medical apparatus and a communication method for the capsule-type medical apparatus, which prevent an increase in the number of digits of the identifier, and can certainly maintain the correspondence between the capsule and external apparatus even when a plurality of patients have swallowed capsules.

The capsule-type medical apparatus relating to the present invention comprises a capsule body, which is inserted in the living body and performs medical procedures such as observation, and an external apparatus which is disposed outside the living body, and further comprising:

sending means established in the abovementioned external apparatus for sending the identifier to the abovementioned capsule body for identifying the capsule body;

first storing means established in the abovementioned external apparatus for storing the identifier information sent by the abovementioned sending means;

receiving means established in the abovementioned capsule body for receiving the identifier sent by the abovementioned sending means; and second storing means established in the abovementioned capsule body for storing the abovementioned identifier information which was sent.

Also, the communication method for a capsule-type medical apparatus relating to the present invention is a communication method for the capsule-type medical apparatus for communicating between a capsule body, which is inserted in the living body and performs medical procedures such as observation, and an external apparatus which is disposed outside the living body, and comprising:

a first step for sending the identifier, for identifying the capsule body, from the abovementioned external apparatus to the abovementioned capsule body and storing the abovementioned identifier information;

a second step for receiving the identifier sent by the abovementioned sending means on the capsule body side; and a third step wherein the abovementioned capsule body stores the identifier received in the second step.

The above and other objects, features, and advantages of the invention will become more clearly understood from the following description referring to the accompanied drawings.

DESCRIPTION OF THE PREFERRED EMBODIMENTS

The preferred embodiments of the present invention are explained below with reference to the drawings.

First Embodiment

Figure 1:
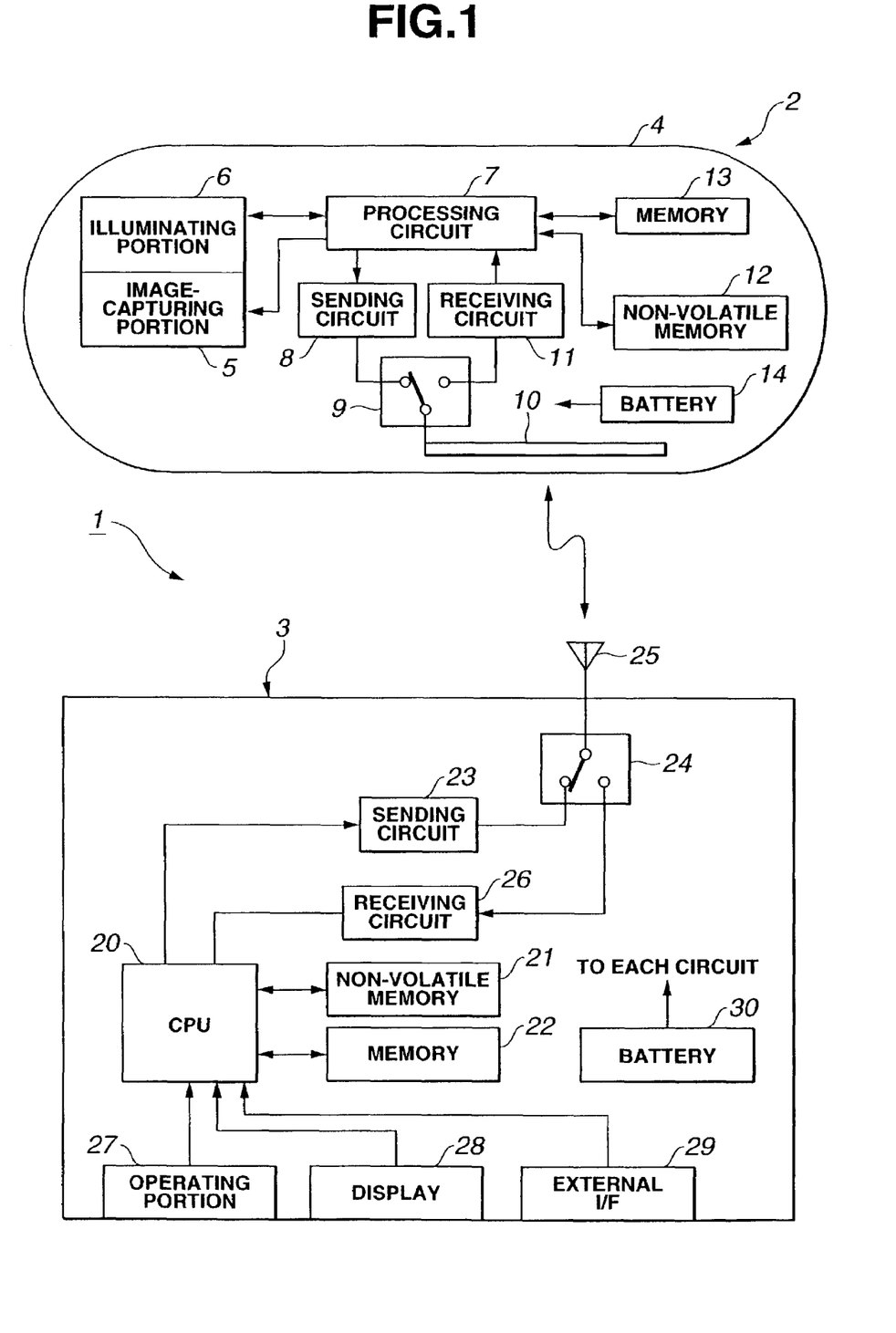
FIG. 1 is a schematic drawing showing the overall constitution of a capsule-type endoscope apparatus relating to a first embodiment of the present invention.
Figure 2A:
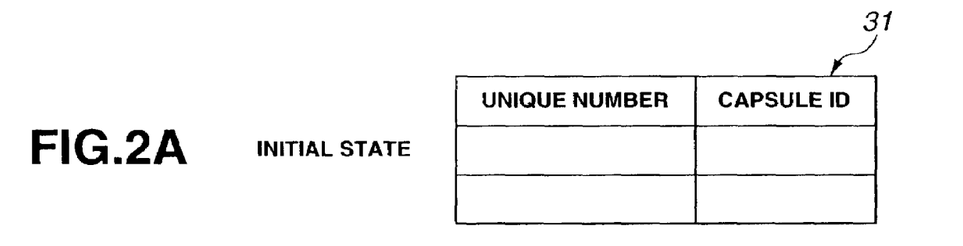
FIG. 2A through FIG. 2E are drawings showing the unique number and capsule ID stored in a management table.
Figure 2B:
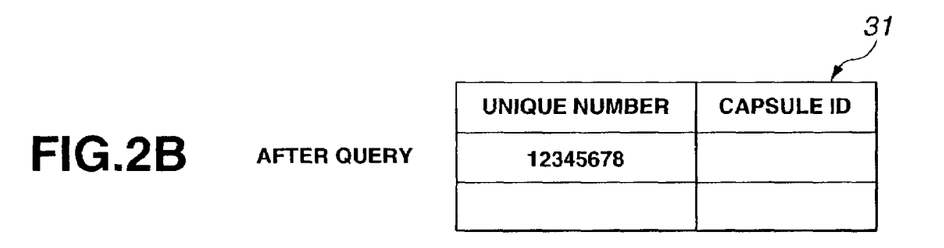
Figure 2C:
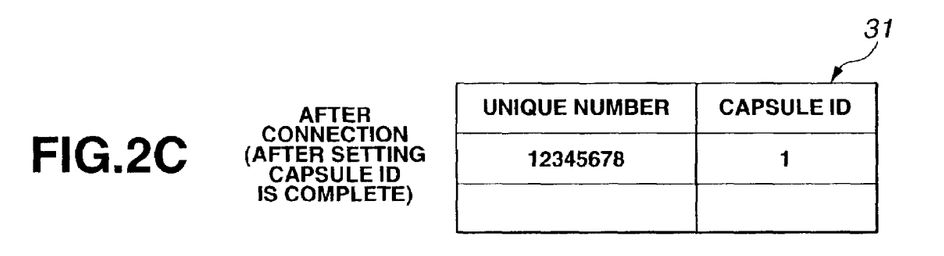
Figure 2D:
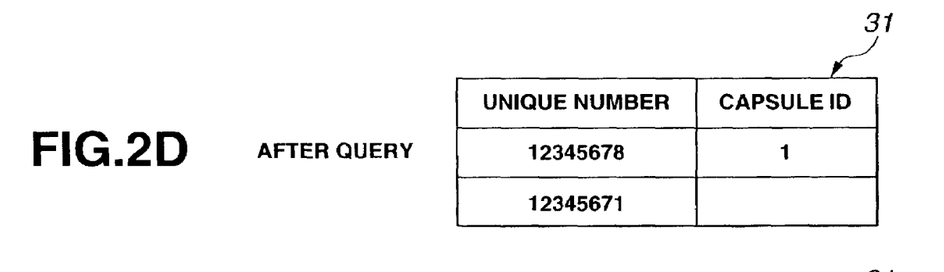
Figure 2E:
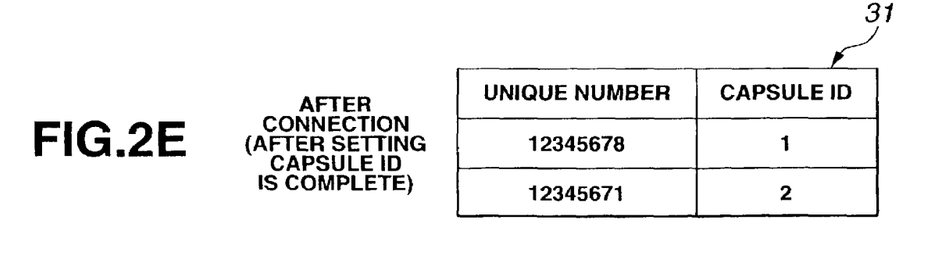
Figure 3A:
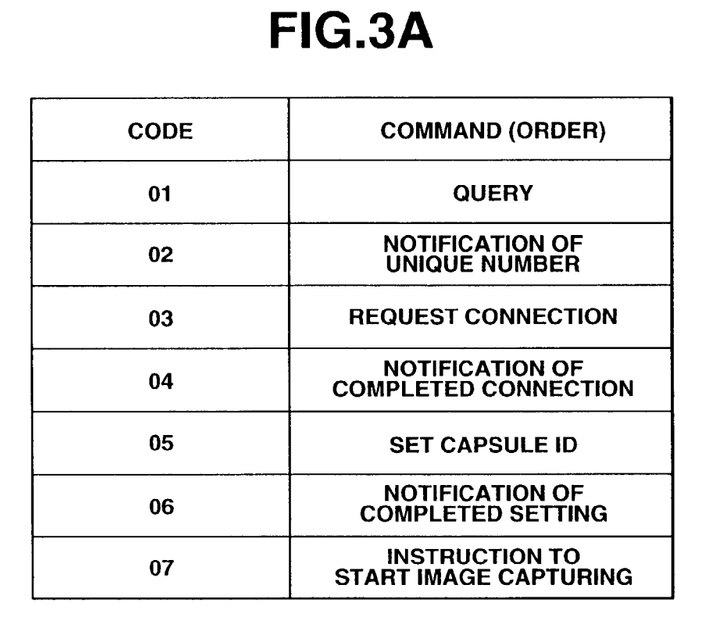
FIG. 3A and FIG. 3B are drawings showing a specific example and the sending and receiving of commands as control information used when performing communication between the external apparatus and the capsule.
Figure 3B:
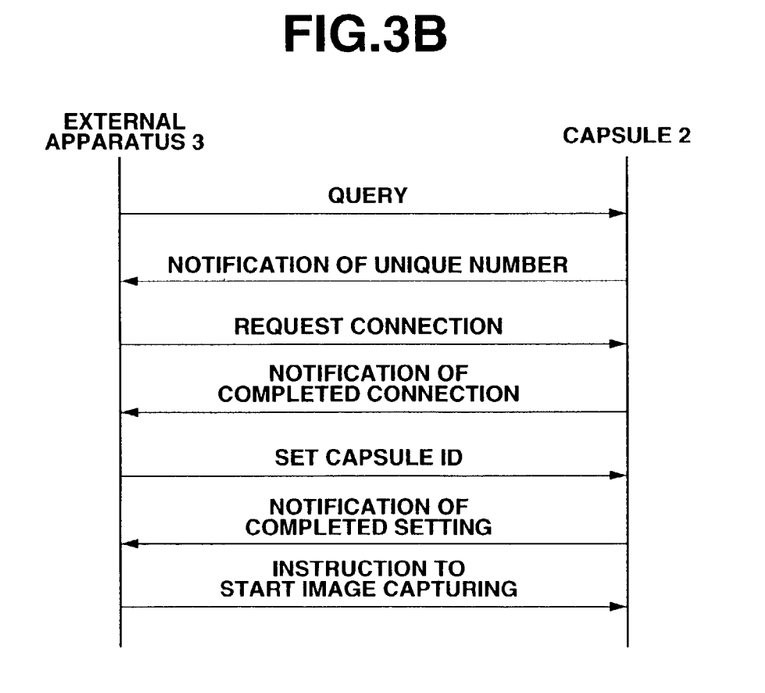
Figure 4:
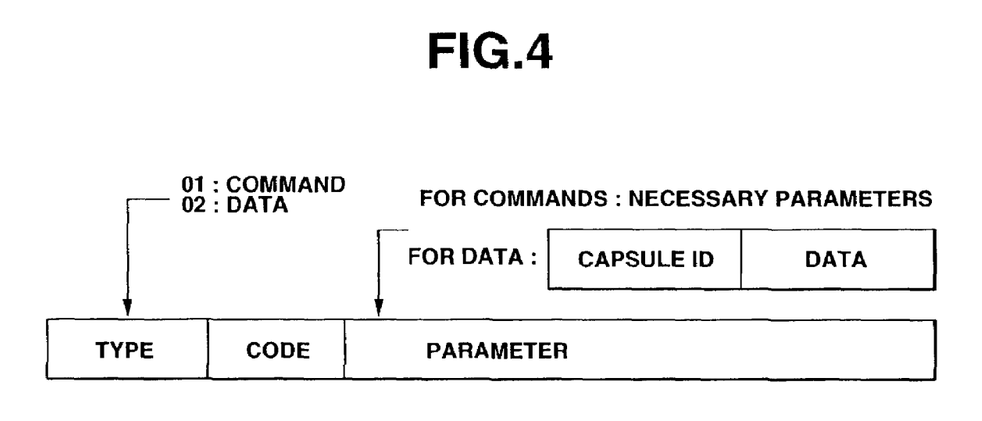
FIG. 4 is a drawing showing a specific example of the formatting when sending control information as a packet.
Figure 5:
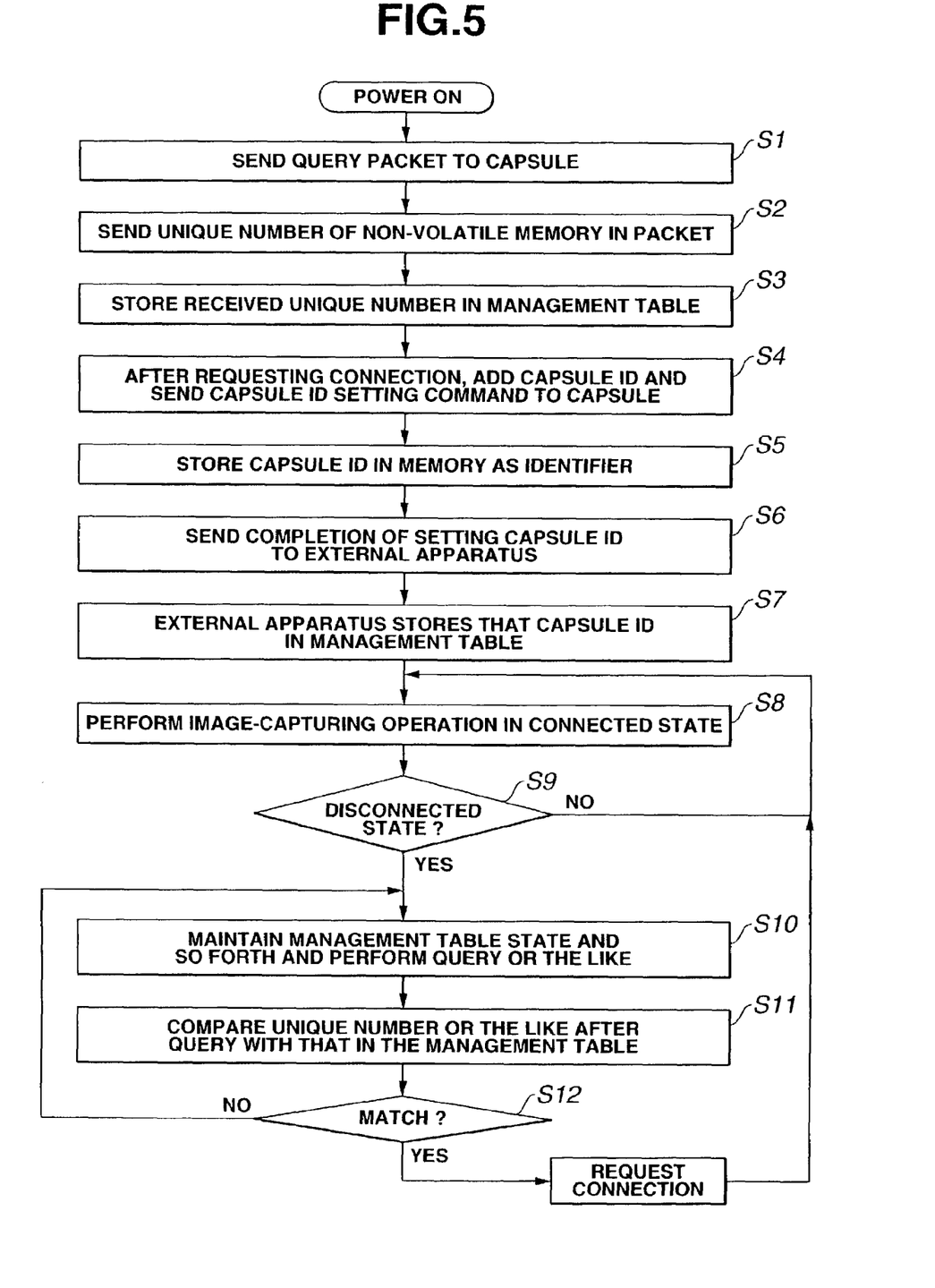
FIG. 5 is a flow chart of the operation of the embodiment.
Figure 6:
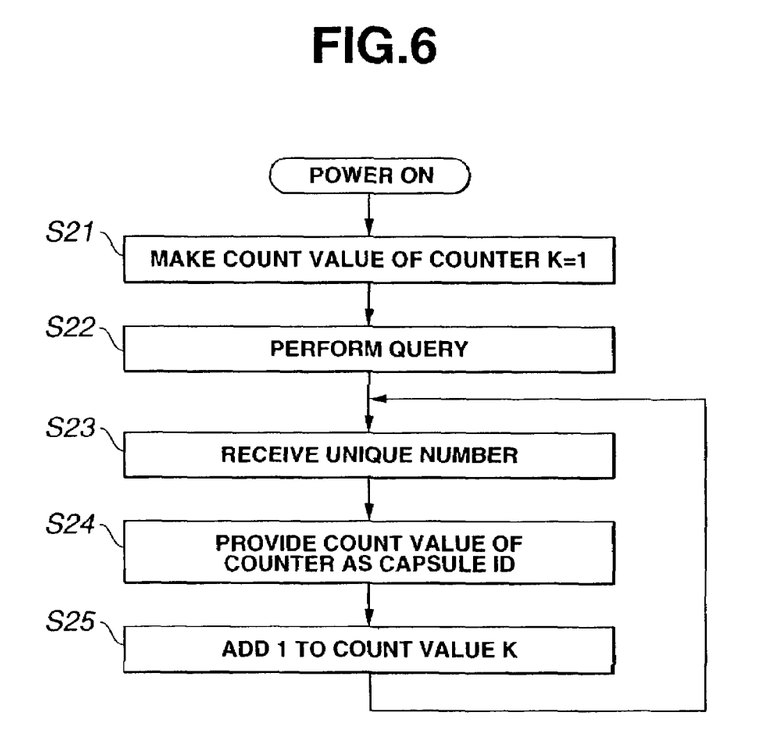
FIG. 6 is a flow chart of the operation for setting the capsule ID.

FIGS. 1 through 6 relate to the first embodiment of the present invention. FIG. 1 is a schematic drawing showing the overall constitution of the capsule-type endoscope apparatus relating to a first embodiment; FIG. 2A through FIG. 2E show the unique number and capsule ID stored in a management table; FIG. 3A and FIG. 3B show a specific example of a command as control information used when performing communication between the external apparatus and the capsule; FIG. 4 shows the formatting when sending control information as a packet; FIG. 5 is a flow chart of the operation of the present embodiment; and FIG. 6 is a flow chart of the operation for setting the capsule ID.

The capsule-type endoscope apparatus 1, relating to the first embodiment of the capsule-type medical apparatus of the present invention shown in FIG. 1, comprises a capsule-type endoscope (hereinafter "capsule") 2 in the form of a capsule so as to be swallowed easily by a patient, and an external apparatus 3 disposed outside the living body of the patient.

The capsule 2 comprises the following: an image-capturing portion 5 for performing image pickup and a lighting portion 6 for lighting the image capturing range for performing image pickup, for example, as the living-body information detecting means for attaining living-body information inside the capsule-shaped, sealed container 4; a processing circuit 7 for signal processing as well as for controlling the image-capturing portion 5 and lighting portion 6; a sending circuit 8 for converting the processed image data and the like into a signal to be sent; a switch 9 having the function of a sending and receiving switching circuit for switching and outputting a high frequency signal from the sending circuit 8; an antenna 10 for the radio wave emission of the high frequency signal which passes through the switch 9; a receiving circuit 11 for receiving the signal received by the antenna 10 through the switch 9 and outputting the demodulated signal to the processing circuit 7; non-volatile memory 12 for storing the unique number from when the capsule 2 was manufactured, a serial number, for example; memory 13 for storing the capsule ID sent from the external apparatus 3; and a battery 14 for supplying operating power to the image-capturing portion 5, lighting portion 6, processing portion 7, sending circuit 8, receiving circuit 11, non-volatile memory 12, and memory 13.

When the living-body information captured by the image-capturing portion 5 is sent through the sending circuit 8, the capsule 2 sends the information with a packet including the capsule ID. However, when the serial number is used as the identifier as explained in the section on the prior art, the quantity of information in the identifier becomes too great. Therefore, in order to determine the capsule ID for the capsule 2 (as an identifier constituted of a small amount of information), the capsule 2 will send the unique number stored in the non-volatile memory 12 to the external apparatus 3.

In the external apparatus 3, the unique numbers of the capsules 2 communicating with the external apparatus 3 are received, a capsule ID constituted of a small amount of information is determined, to make it possible to identify each capsule 2 which is in communication, and the capsule ID is sent to the capsule 2.

The abovementioned capsule 2 receives the capsule ID sent from the external apparatus 3, stores the capsule ID of the capsule ID in the memory 13, and uses the capsule ID stored in the memory 13 as the capsule ID for identifier information for identifying the capsule 2.

Meanwhile, the abovementioned external apparatus 3 comprises the following: a CPU 20 for controlling each circuit in the external apparatus 3; non-volatile memory 21 connected with the CPU 20, and storing image data and so forth sent from the capsules 2, along with a management information for managing all of the capsules 2 for performing communication; memory 22 for storing image information and so forth; a sending circuit 23 for sending the capsule ID and so forth to the capsule 2 according to the management information in the non-volatile memory 21; a switching circuit 24 having the function of the sending and receiving switching circuit when sending the signal from the sending circuit 23 connected; an antenna 25 for emitting in radio wave the signal sent from the sending circuit 23 through the switching circuit 24; a receiving circuit 26 for inputting through the switching circuit 24 a signal received with the antenna 25; an operating portion 27 (provided with a plurality of keys (buttons)) used when performing control operations of the capsule 2 from the external apparatus 3; a display 28 for displaying information and so forth operated by the operating portion 27; an external interface 29 provided with serial communication means or the like, such as USB, which makes it possible to connect with an external personal computer or the like and transfer image information stored in memory 22; and a battery 30 for supplying operating power to each circuit such as the CPU 20 in the external apparatus 3.

The abovementioned external apparatus 3 forms a management table 31 as shown in FIG. 2A through FIG. 2E inside the non-volatile memory 21. This management table 31 comprises a unique number storing portion, for storing the unique numbers sent from the capsules 2 used actually in combination therewith, and a storing portion for capsule IDs allocated (provided) as identifiers with respect to those unique numbers.

Moreover, the external apparatus 3 forms a management table 31 with the non-volatile memory 21 in order to retain the information in the management table 31 without loss when the power is turned off or is reset.

Nothing is stored in this management table 31 in the initial state shown in FIG. 2A, but when the external apparatus 3 is powered on, the CPU 20 of the external apparatus 3 sends in packets a query command associated with control information.

As shown in FIG. 3A, this control information includes commands (orders) for queries, notification of the unique number, connection requests, notification of completed connection, setting the capsule ID, notification that setting is complete, and instructions to start image capturing; those being corresponded to codes 01 through 07 for example.

These codes 01 through 07 are registered as a code table in the non-volatile memory 12 of the capsule 2 and the non-volatile memory 21 of the external apparatus 3. A code in the code block of a received packet is compared and referenced to check for correspondence with a code stored in the code table; and it can be determined to which command in FIG. 3A the control information sent corresponds.

In effect, the code table has the functions of encoding means for converting commands to be sent to the corresponding (command) code, and of decoding means for converting the received (command) code back into the corresponding command.

The sending and receiving of each command in FIG. 3A becomes as shown in FIG. 3B.

In effect, a query command goes from the external apparatus 3 to the capsule 2; a unique number notification command goes from the capsule 2 to the external apparatus 3; a connection request command goes from the external apparatus 3 to the capsule 2, and so on. Moreover, the response to the query command may be only the notification of the unique number, but as discussed below, the capsule ID may be returned along with the unique number when the capsule ID has been set.

When power is first turned on, for example, the external apparatus 3 sends a query command to the capsule 2. The capsule 2 then receives the query command, determines that it is a query command, and sends the unique number stored in the non-volatile memory 12.

In this case, the packet or data are sent in the packet format as shown in FIG. 4.

Specifically, this format is divided into the following regions: the type of command or data, the code (blank or space in the case of data) in the case of a command, and the parameters. The type is 01 in the case of a command and 02 in the case of data.

In the case of a command, the parameter region includes settings for necessary information for that command. For example, when a control command is sent from the external apparatus 3 to a specific capsule 2, the capsule ID which is the identifier of the capsule 2 is designated in the parameter region. If a capsule ID is not designated in the parameter region, the control command is for all of the capsules 2.

In the case of data, the capsule ID of the sender and the data sent are stored in the parameter region.

Moreover, when the capsule ID is not provided, the unique number is used instead of the capsule ID. When the setting of the capsule ID is complete, the capsule ID is used subsequently thereto.

In this way, the capsule 2 sends its unique number in response to the sending of a query command or a query.

The CPU 20 of the external apparatus 3 stores the unique number received in the management table 31 as shown in FIG. 2B. Thereafter, the external apparatus 3 makes a connection request to the capsule 2 with that unique number and sends a command to set the capsule ID to the capsule 2 with which it is connected.

In this case, the unique number and capsule ID are designated in the parameter region. The designated capsule ID is set along with the unique number to the capsule 2 with that unique number. Specifically, the capsule 2 with that unique number stores the capsule ID sent in its internal memory 13.

When this capsule ID is stored, the capsule is placed in the state of using the capsule ID as an identifier and sends the command to make notification that the setting is complete to the external apparatus 3.

After making a connection to the capsules 2 with unique numbers and after setting is complete, the capsule IDs are related to the unique numbers and stored in the management table 31 of the external apparatus 3 as shown in FIG. 2C.

FIG. 2B and FIG. 2C show the setting of a capsule ID for one capsule. In the case of two capsules 2, query processing is further performed and after the query, the second unique number is stored in the management table 31 as shown in FIG. 2D. After the connection is made (after the setting of the second capsule ID is complete), the capsule ID is related to the unique number and is set for the second capsule 2 as shown in FIG. 2E.

The operation of the present embodiment is explained next with reference to FIG. 5.

First, power is turned on. In this case, the external apparatus 3 is powered on after the capsule 2 is powered on.

Thereupon, in step S1, the CPU 20 of the external apparatus 3 sends a query packet, to query whether a capsule 2 is present in the vicinity, from the sending circuit 23.

As shown in step S2, the capsule which received the query packet identifies the command and sends the unique number (written when the capsule 2 was manufactured or the like) in a packet through the sending circuit 8 to the external apparatus 3.

As shown in step S3, the external apparatus 3 takes up the response packet from the capsule 2 through the receiving circuit 26 into the CPU 20, extracts the unique number from that packet, and writes the unique number to the management table 31 in the non-volatile memory 21 as shown in FIG. 2B.

As shown in step S4, the external apparatus 3 makes a connection request to the capsule 2 with the unique number acquired, applies the capsule ID, and sends the capsule ID setting command in a packet to the capsule 2.

As shown in step S5, the capsule 2, (with the abovementioned unique number), which received the capsule ID setting command wherein the capsule ID designating a unique number is added, stores the capsule ID sent with the capsule ID setting command in the memory 13 and subsequently enters a state of using the capsule ID as an identifier.

As shown in step S6, the capsule 2 sends the command of which capsule ID setting is complete to the external apparatus 3, with the capsule ID added.

As shown in step S7, the external apparatus 3 receives the command of which capsule ID setting is complete, relates the unique number and capsule ID, and stores this information to the management table 31 as shown in FIG. 2C.

The setting operation of the capsule ID to one capsule 2 is thereby completed; and it becomes possible to operate the operating portion 27 of the external apparatus 3, such that a command is sent to the capsule 2 for carrying out instructions for the image-capturing operation or the like, and control for causing the capsule 2 to perform image capturing or the like is performed.

When two or more capsules are used in combination by the external apparatus 3, the processing from step S1 through step S7 is completed for the first capsule 2. The second capsule 2 is then powered on, and the capsule ID can be provided to the second capsule 2 in the same way by operating the operating portion 27 of the external apparatus 3, sending the query packet in step S1, and repeating the processing up to step S7.

FIG. 6 is a flow chart to explain the operation for providing capsule IDs with a small number of bits in the case of a plurality of capsules 2.

In the case where the external apparatus 3 is powered on and then sends the query command packet and receives the unique number notification from a plurality of capsules 2, the CPU 20 counts the capsule IDs in order from the capsule 2 which initially received a unique number with the counter in the CPU 20, and generates identifier information which does not overlap. At that time, the number of digits of the counter is determined to be the number of digits so as not to overflow with the number of capsules swallowed at once.

As shown in FIG. 6, when power is turned on, the count value K of the counter is set to 1, the initial state, as shown in step S21. The query command in the next step S22 is then sent to the capsule 2.

In the next step S23, the unique number initially sent from the capsule 2 is received following the query. After the reception of that unique number, the count value K (=1) of the counter becomes the capsule ID in the next step S24. The capsule ID is then sent to the capsule 2 which initially sent the unique number; and the capsule ID is provided as the identifier.

In the next step S25, the count value K of the counter is increased by +1, and the process returns to step S23, the next unique number is received, and the same process is performed. By processing in this way, identifiers with a small number of bits can be handled even in the case of a plurality of capsules.

Even when setting the capsule IDs in such a case with a plurality of capsules, the capsule IDs are provided in relation to the unique numbers and if the unique numbers such as serial numbers are different, different capsule IDs will be provided without fail and the quantity of information in the capsule IDs in that case will be low. Therefore, in subsequent communications, the quantity of information in the capsule ID does not cause a reduction in transmission efficiency.

As discussed above, the capsule is placed in the state of performing the image-capturing operation with the completion of the setting of the capsule ID, by setting the connected state and sending the instruction to start image capturing as shown in step S8 in FIG. 5. With this image-capturing operation, the capsule 2 sends the captured image data to the external apparatus 3, and the external apparatus 3 stores the image data received in the memory 22.

Moreover, in the present embodiment, the capsule 2, which was instructed by the instruction to start image capturing, is caused to continue the image-capturing operation. The capsule may be caused to perform the operation of image capturing for just one frame, for example, by the instruction to start image capturing, and this mode of the embodiment is discussed below.

When the capsule 2, which was instructed by the instruction to start image capturing, performs image capturing and sends the captured image data, the capsule ID sent is attached as shown in FIG. 4. Therefore, the capsule 2 from which the information was sent can be identified with certainty even when the external apparatus 3 is temporarily using a plurality of capsules 2 in combination.

After the start of the image-capturing operation shown in step S8, the CPU 20 of the external apparatus 3 determines whether the connection is in disconnected state as shown in step S9.

For example, when interfering radio waves such as noise come through and the communication quality becomes bad, it is then determined whether the connection has become a disconnected state. In the case of a connected state, the process returns to step S8 and the capsule enters a state of performing the image-capturing operation.

On the other hand, in the case of a disconnected state, the external apparatus 3 maintains the status of the management table 31 in the non-volatile memory 21, and the capsule 2 maintains the capsule ID in the memory 13, as shown in step S10. The external apparatus 3 then resends the query packet and the capsule 2 sends the unique number along with the capsule ID in a packet to the external apparatus 3 through the sending circuit 8.

As shown in step S11, the external apparatus 3 which received the unique number and capsule ID compares that information with the information stored in the management table 31.

As shown in step S12, it is determined whether that information matches. If there is a match, it is decided that the connectable state was recovered, and a connection request is made, and the process is returned to step S8 to make it possible to proceed with the image-capturing operation.

On the other hand, if there is no match, it is decided that this is a disconnected state due to noise or the like, and the process is returned to step S10 and returns to query processing and so forth.

The present embodiment has the following effects.

It is not necessary to provide a switch for providing a capsule ID to the capsule 2. Also, it is not necessary to provide a unique number in the header of a packet. Just by setting a capsule ID, each capsule 2 can find packets addressed to itself, while the external apparatus 3 can identify the capsule 2 from which a packet was sent.

Also, the capsule ID may identify the capsules 2 swallowed, and because the quantity of information amounts to several bits, there is no reduction in transmission efficiency. The original living-body information attained with the capsule 2, specifically the image information captured thereby, can be sent with good efficiency, while the capsule from which the image information was sent can be identified. Furthermore, even when the connected state between the capsule 2 and external apparatus 3 is lost, a mistaken connection with another capsule 2 can be prevented.

Second Embodiment

The second embodiment relating to the present invention is explained next with reference to FIGS. 7 and 8. In the present embodiment, when the capsule 2 actually used with the external apparatus 3 is mistakenly set with the identifier of another capsule 2, it is possible to delete that identifier.

Figure 7:
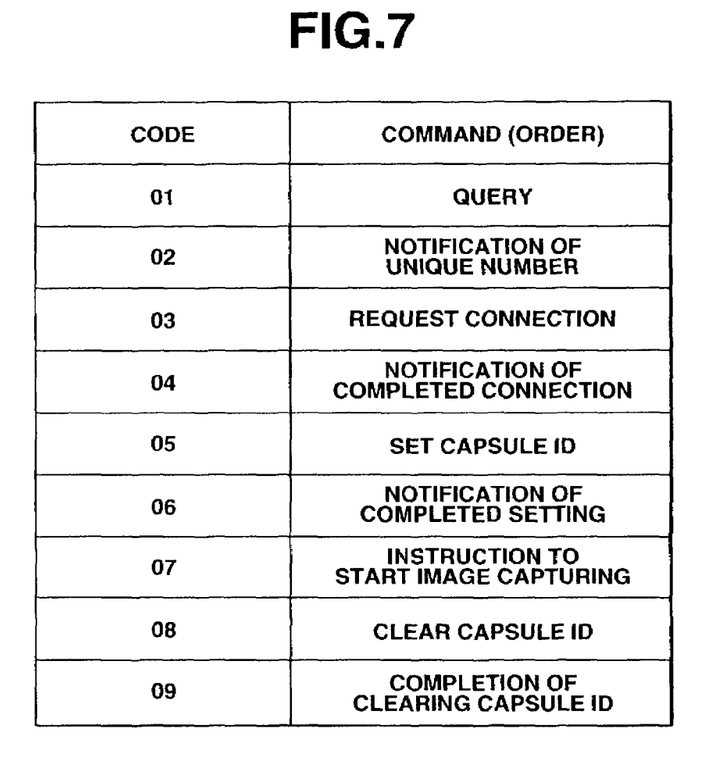
FIG. 7 is a drawing showing a specific example of commands in a second embodiment of the present invention.

The present embodiment further includes additional types of commands as shown in FIG. 7, in addition to those in the first embodiment. The commands, a capsule ID clear command and a completion of clearing capsule ID command as codes 08 and 09, are added to the commands from 01 to 07 in the first embodiment.

Consequently, as the control packet, codes for the following are registered as the 01 through 09 code table in the non-volatile memories 21 and 12 of the external apparatus 3 and capsule 2 respectively: queries, notification of the unique number, connection requests, notification of completed connection, setting the capsule ID, notification that setting is complete, instructions to start image capturing, capsule ID clear, and completion of clearing capsule ID.

The code region on the received control packet is then compared and referenced with the code table, and the CPU 20 in the external apparatus 3 and the processing circuit 7 in the capsule 2 execute the processing to be performed.

Figure 8:
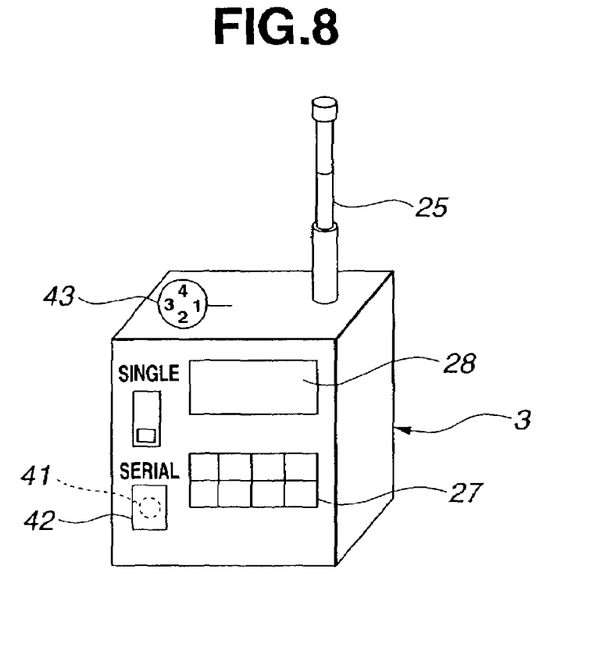
FIG. 8 is a perspective view showing the external apparatus including a capsule ID clear button so forth.

Also, in the present embodiment, a capsule ID clear button 41 is established on the external apparatus 3 as shown in FIG. 8. The capsule ID clear command is issued only when this button 41 is pressed.

In this case, a cover 42 is established so that the button 41 is not mistakenly pressed as an emergency bell button. When this capsule ID clear button 41 is operated, a capsule ID clear command is sent from the external apparatus 3, and a completion of clearing capsule ID command is received from the capsule 2, then the external apparatus 3 returns the management table 31 to its initial state.

Also, in the state where the external apparatus 3 can use a plurality of capsules 2, a capsule ID selecting switch 43 may also be established on the external apparatus 3. This capsule ID selecting switch 43 is rotated, or the like, the capsule ID to be deleted is selected, and the capsule ID clear button 41 is operated.

Thereupon, the capsule ID, indicating the capsule ID for which deletion was selected, is placed in the parameter region of the capsule ID clear command packet, and is sent to the capsule 2 from the external apparatus 3.

The capsule ID of the capsule 2 having the capsule ID matching with the specified capsule ID is cleared and the completion of clearing capsule ID command is received from the capsule 2. The external apparatus 3 receives this and deletes the capsule ID from the management table 31.

Accordingly, even when a plurality of capsules 2 are used in combination by a single external apparatus 3, it is certainly possible to return only a mistakenly set capsule 2 to the initial state of being not used.

Consequently, the present invention includes the following effect in addition to the effects of the first embodiment: when an identifier is set for a capsule 2 which is not actually being used, it is possible to delete the identifier set for the capsule 2 and to set identifiers only for capsules 2 which are actually used.

Third Embodiment

Figure 9A:
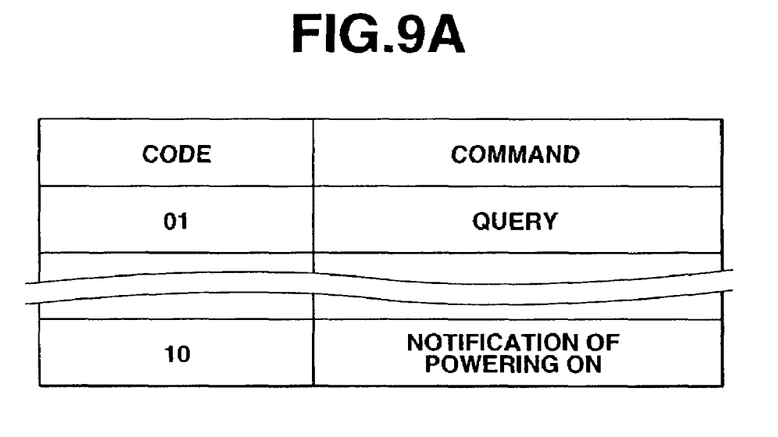
FIG. 9A through FIG. 9C show commands and the sending and receiving directions or the like in a third embodiment of the present invention.

The third embodiment relating to the present invention is explained next with reference to FIG. 9A through FIG. 9C. In addition to the second embodiment, for example, the present embodiment is further provided with a command for giving notification of powering on, to give notification when power is supplied to a capsule 2 as shown in FIG. 9A.

Figure 9B:
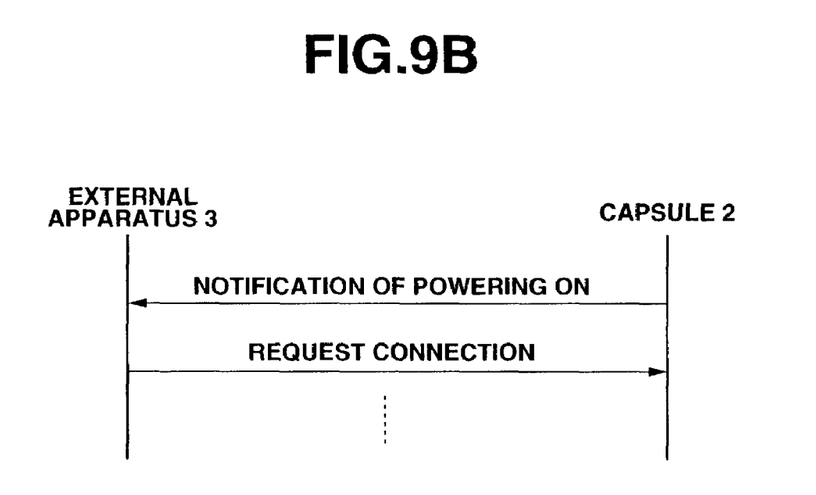

This command is sent from the capsule 2 to the external apparatus 3 as shown in FIG. 9B.

In this case, the notification is sent to the external apparatus 3 in a packet for giving notification that power is applied to a capsule 2, in the format explained in FIG. 4.

Figure 9C:
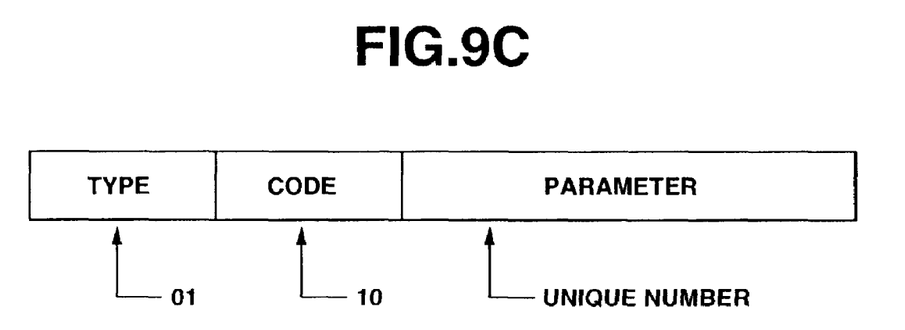

Specifically, this is sent in the format as shown in FIG. 9C. In effect, the type of header is 01, the code is 10 in this case, and the unique number is added (designated) as the parameter.

In the present embodiment, the capsule 2 executes the notification of powering on, while giving notification of its unique number at that time. As a result, the external apparatus 3 next sends the connection request command (without sending a query command) and is able to perform the setting of the capsule ID for the capsule 2.

With the addition of the command for notification of powering on, the present embodiment can broaden the selection alternatives in the case where the external apparatus 3 and capsule 2 are used in combination, and can further improve operability.

For example, when the external apparatus 3 is paired with a single capsule 2, and during the operations thereof, power is applied to another capsule 2 which is provided with different functions or the like, another capsule ID can be set for the capsule 2 thereafter. In effect, operability can be improved.

Fourth Embodiment

The fourth embodiment of the present invention is explained next with reference to FIG. 10A and FIG. 10B. In the first embodiment, when the instruction to start image-capturing command is sent to the capsule 2, the capsule 2 then maintains the state of image capturing. On the other hand, in the present embodiment, when the instruction to start image-capturing command is sent to the capsule 2, the capsule 2 which was instructed to start image capturing sends image information for one frame.

Consequently, the present embodiment basically has the same constitution as the first embodiment, and the processing relating to the instruction to start image-capturing command is different in part.

Figure 10A:
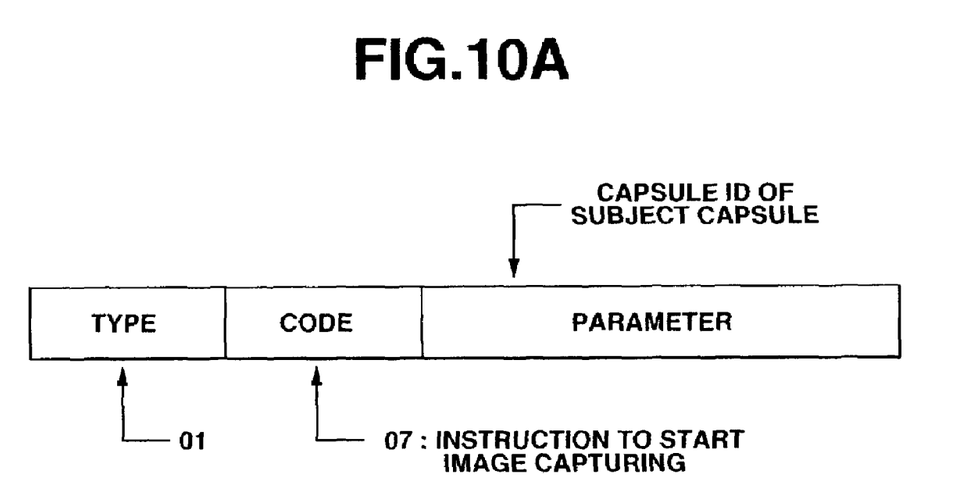
FIG. 10A and FIG. 10B show the packet format and so forth in the case of sending a command instructing the capsule to start image capturing in a fourth embodiment of the present invention.

The packet of the instruction to start image capturing becomes as shown in FIG. 10A in this case. In effect, the type of header is 01, the code is 07 in this case, and the capsule ID of the capsule 2, which is subject to perform image capturing, is designated as the parameter.

Figure 10B:
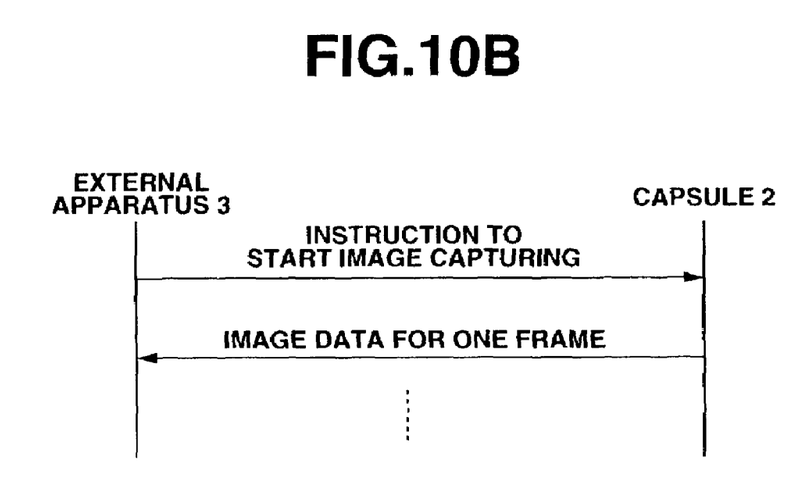

With the sending of a packet including the instruction to start image-capturing command from the external apparatus 3 to the capsule 2 as shown in FIG. 10B, that packet is received, and that designated capsule ID performs an operation of capturing a single frame image and sending that image data for one frame.

With the present embodiment, the image-capturing operation can be performed at locations where image capturing is actually necessary, because image capturing and the sending of image information are performed only when image capturing is instructed. Consequently, even when the battery 14 of the capsule 2 is small and contains a small amount of electrical energy, the capsule 2 can be used for a long period of time without wasteful consumption of energy.

Fifth Embodiment

The fifth embodiment of the present invention is explained next with reference to FIG. 11, FIG. 12A, and FIG. 12B. The present embodiment is the fourth embodiment with the addition of a command to initiate serial image capturing.

Figure 11:
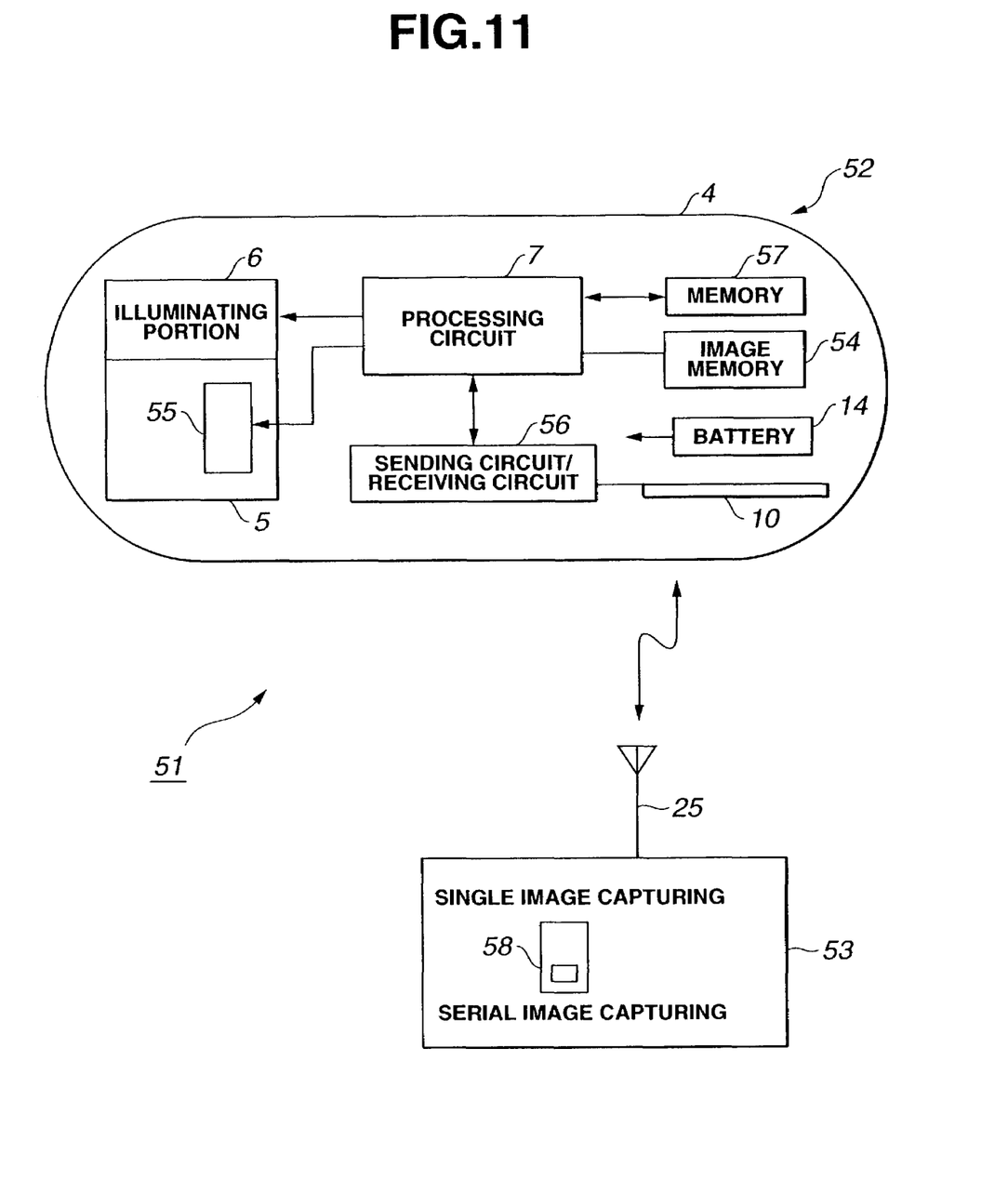
FIG. 11 is a schematic drawing of the constitution of the capsule-type endoscope apparatus relating to a fifth embodiment of the present invention.

The capsule-type endoscope apparatus 51 relating to the fifth embodiment and shown in FIG. 11 comprises a capsule 52 and an external apparatus 53 used in combination with this capsule 52. The capsule 52 further includes an image memory 54, for storing image data, for a plurality of frames in the capsule 2 in FIG. 1.

In the present embodiment, a CMOS imager (image pickup device) 55 is employed as an image pickup element established in a location for capturing images with an objective optical system in the image-capturing portion 5, for example. Also, for the sake of simplicity in FIG. 11, the sending circuit 8, switch 9, and receiving circuit 11 in FIG. 1 are shown with a sending and receiving circuit 56, and the non-volatile memory 12 and memory 13 in FIG. 1 are shown with a memory portion 57. Otherwise, the constitution is the same.

The external apparatus 53 has basically the same constitution as the external apparatus 3 shown in FIG. 1. Furthermore, a selecting switch 58 is established for selecting and setting the operating mode between the single frame image-capturing mode and multi-frame serial image-capturing mode.

Figure 12A:
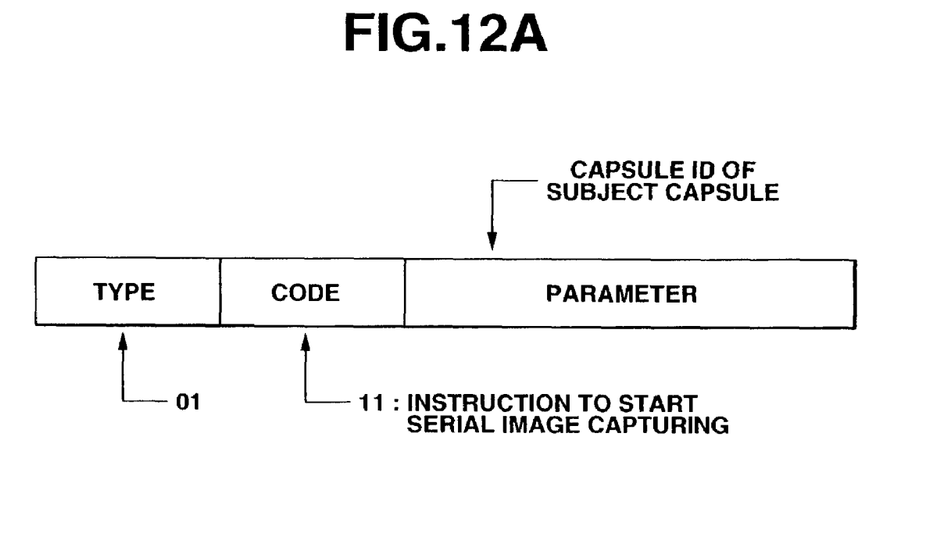
FIG. 12A and FIG. 12B show the packet format and so forth in the case of sending a command instructing the capsule to start serial image capturing.

FIG. 12A shows the packet format in the case of sending the instruction to start serial image-capturing command.

In effect, the header type is 01, the code is 11 in this case, and the capsule ID of the capsule subject to perform image capturing is designated as the parameter.

Figure 12B:
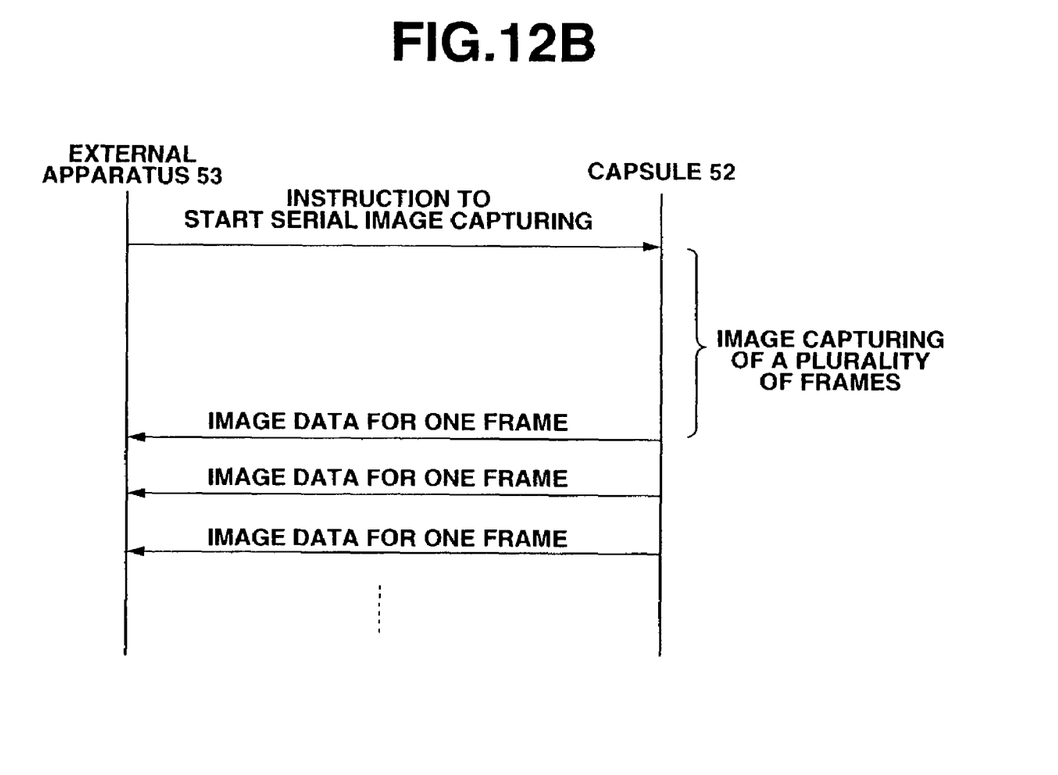

As shown in FIG. 12B, with the sending of the command giving the instruction to start serial image capturing to the capsule 52, the capsule 52 performs serial image capturing of a plurality of frames, in effect the number of frames that can be stored in the image memory 54, and then sends the image data stored in the image memory 54, sequentially, as image data for single frame, to the external apparatus 53.

In the present embodiment, the performance of serial image capturing is further added to the fourth embodiment and therefore this embodiment can correspond more broadly to user needs and the usability is improved.

Moreover, an operating-mode storing region for storing the operating mode is established in the memory 22 or non-volatile memory 21 (shown in FIG. 1) of the external apparatus 53. The external apparatus 53 is connected to an external personal computer through the external interface 29 (shown in FIG. 1), and the operating mode may also be set by performing the operation for setting the operating mode from the personal computer.

Moreover, in the embodiments discussed above, a situation was explained wherein image information was obtained as means for performing medical procedures such as to attain living-body information with the capsule 2. However, the present invention is not limited by this and may also be a capsule-type medical apparatus employing a pH sensor, a temperature sensor, a pressure sensor, a photo sensor, or a blood sensor, as noted in Japanese Patent Application 2001-341101 from paragraph number 88 onward, or may include an ultrasound probe instead of the various sensors, or may perform drug dispersion, body fluids collection, or drug injection functions.

Having described the preferred embodiments of the invention referring to the accompanied drawings, it should be understood that the present invention is not limited to these precise embodiments and various changes and modifications thereof could be made by one skilled in the art without departing from the spirit or scope of the invention as defined in the appended claims.

What is claimed is:

1. A capsule-type medical apparatus comprising a capsule body, inserted in a living body and performing medical procedures such as observation, and an external apparatus disposed outside the living body, and further comprising:

an image-capturing portion for capturing an image of a subject to output an image-capturing signal, the image-capturing portion being provided to the capsule body;

capsule sending means, established in the capsule body, for sending to the external apparatus a first identifier stored in the capsule body for identifying the capsule body;

external apparatus receiving means, established in the external apparatus, for receiving the first identifier;

external apparatus sending means, established in the external apparatus, for sending to the capsule body a second identifier related to the first identifier and having a smaller number of bits than the first identifier;

first storing means, established in the external apparatus, for storing information of the second identifier sent by the external apparatus sending means;

capsule receiving means, established in the capsule body, for receiving the second identifier sent from the external apparatus sending means;

second storing means, established in the capsule body, for storing the information of the second identifier sent from the external apparatus sending; means and a processing circuit for generating a signal having the second identifier added to the image-capturing signal and sending the image-capturing signal with the second identifier added thereto generated by the processing circuit to the external apparatus receiving means via the capsule sending means.

2. The capsule-type medical apparatus according to claim 1, wherein the capsule body comprises means for storing a unique number such as a serial number.

3. The capsule-type medical apparatus according to claim 2, wherein the capsule body sends said unique number to the external apparatus, and the external apparatus sends to the capsule body the second identifier according to said unique number.

4. The capsule-type medical apparatus according to claim 3, further comprising means for designating the capsule body for which the second identifier is to be deleted.

5. The capsule-type medical apparatus according to claim 1, further comprising means for providing different second identifiers to a plurality of capsule bodies.

6. The capsule-type medical apparatus according to claim 5, wherein a counter circuit is used as means for providing different second identifiers.

7. The capsule-type medical apparatus according to claim 1, wherein the capsule body comprises image-capturing means; and the capsule body executes the acquisition of data and the sending of data at instructions from the external apparatus.

8. The capsule-type medical apparatus according to claim 7, wherein the data acquired are image data and image data are sent.

9. The capsule-type medical apparatus according to claim 8, wherein image data for one frame is captured at a single instruction; and an image of one frame is sent.

10. The capsule-type medical apparatus according to claim 8, wherein the capsule body comprises a frame memory, captures image data for a plurality of frames at a single instruction, stores image data corresponding to a plurality of frames in frame memory, and performs wireless transmission of the image data stored in frame memory.

11. The capsule-type medical apparatus according to claim 8, comprising selecting means for selecting between the case where image data for one frame is captured at a single instruction and an image of one frame is sent, and the case where image data for a plurality of frames is captured at a single instruction and image data for a plurality of frames is sent.

12. A communication method for a capsule-type medical apparatus for communicating between a capsule body, inserted in a living body and performing medical procedures such as observation, and an external apparatus disposed outside the living body, and comprising:
　a first step for sending from the capsule body to the external apparatus a first identifier stored in the capsule body for identifying the capsule body;
　a second step in which the external apparatus receives the first identifier sent in the first step;
　a third step in which the external apparatus sends a second identifier related to the first identifier and having a smaller number of bits than the first identifier;
　a fourth step in which the external apparatus stores information of the second identifier;
　a fifth step in which the capsule body receives the second identifier which is sent in the third step;
　a sixth step in which the capsule body stores information of the second identifier;
　a seventh step of capturing an image of a subject and outputting an image-capturing signal, the image-capturing being provided by the capsule; and
　an eighth step in which a signal having the second identifier is added to the image-capturing signal and sending the image-capturing signal with the second identifier added thereto to the external apparatus.

13. The communication method for a capsule-type medical apparatus according to claim 12, further comprising:
　a step for recognizing an interrupted connection between the external apparatus and the capsule body; and
　a step for recovering the paired relationship between the external apparatus and the capsule body.

14. The communication method for a capsule-type medical apparatus according to claim 12, further comprising a step for deleting the second identifier provided to the capsule body.

15. The communication method for a capsule-type medical apparatus according to claim 12, further comprising:
　a step for recognizing the powering on of the external apparatus; and
　a step for providing an identifier from the external apparatus to a capsule body.

16. The communication method for a capsule-type medical apparatus according to claim 12, further comprising:
　a step for recognizing the powering on of the capsule body; and
　a step for providing an identifier from the external apparatus to the capsule body.

17. A capsule-type medical apparatus comprising a capsule body inserted in a living body for performing medical procedures such as observation, and an external apparatus disposed outside the living body, and further comprising:;
　an image-capturing unit for capturing an image of a subject to output an image-capturing signal, the image-capturing unit being provided to the capsule body;
　a first storing area provided in the capsule body for storing a first identifier for identifying the capsule body beforehand;
　a capsule sending unit provided in the capsule body for sending the first identifier to outside of the capsule body;
　an external apparatus receiving unit provided in the external apparatus for receiving signal from the capsule sending unit;
　an external apparatus storing area provided in the external apparatus for storing a second identifier related to the first identifier received by the external apparatus receiving unit and having a smaller number of bits than the first identifier;
　an external apparatus sending unit provided in the external apparatus for sending the second identifier stored in the external apparatus storing area to the outside of the external apparatus;
　a capsule receiving unit provided in the capsule body for receiving signal containing the second identifier sent from the external apparatus sending unit;
　a second storing area provided in the capsule body for storing information of the second identifier received by the capsule receiving unit; and
　a processing circuit for generating a signal having the second identifier added to the image-capturing signal and sending the image-capturing signal with the second identifier added thereto generated by the processing circuit to the external apparatus receiving means via the capsule sending means.

18. A communication method for a capsule-type medical apparatus for communicating between a capsule body, inserted in a living body and performing medical procedures such as observation, and an external apparatus disposed outside the living body, the communication method comprising:
　a first step for the capsule body to send a first identifier for identifying the capsule body stored beforehand in a first storing area therein to the outside from a capsule sending unit:
　a second step for the external apparatus to receive the first identifier sent at the first step by an external apparatus receiving unit;
　a third step for the external apparatus to relate a second identifier having a smaller number of bits than the first identifier to the first identifier received at the second step and store it in an external apparatus storing area;
　a fourth step for the external apparatus to send the second identifier stored at the third step to the outside from an external apparatus sending unit;
　a fifth step for the capsule body to receive the second identifier sent at the fourth step by a capsule receiving unit;
　a sixth step for the capsule body to store information of the second identifier received at the fifth step in a second storing area;
　a seventh step of capturing an image of a subject and outputting an image-capturing signal, the image-capturing being provided by the capsule; and
　an eighth step in which a signal having the second identifier is added to the image-capturing signal and sending the image-capturing signal with the second identifier added thereto to the external apparatus.

* * * * *